(12) United States Patent
Rånby et al.

(10) Patent No.: US 9,665,692 B2
(45) Date of Patent: May 30, 2017

(54) SYSTEM FOR ENABLING TEST DATA FROM A CLINICAL ANALYTIC DEVICE TO BE COMMUNICATED TO AN ELECTRONIC PATIENT INFORMATION MANAGEMENT SYSTEM

(75) Inventors: Mats Rånby, Vreta Kloster (SE); Xerxes Rånby, Vadstena (SE)

(73) Assignee: Zafena AB, Vreta Kloster (SE)

( * ) Notice: Subject to any disclaimer, the term of this patent is extended or adjusted under 35 U.S.C. 154(b) by 989 days.

(21) Appl. No.: 13/818,853

(22) PCT Filed: Aug. 25, 2011

(86) PCT No.: PCT/SE2011/051023
§ 371 (c)(1),
(2), (4) Date: Jun. 5, 2013

(87) PCT Pub. No.: WO2012/026872
PCT Pub. Date: Mar. 1, 2012

(65) Prior Publication Data
US 2013/0241707 A1    Sep. 19, 2013

(30) Foreign Application Priority Data
Aug. 25, 2010  (SE) ...................................... 1050873

(51) Int. Cl.
*G06F 19/00* (2011.01)
*A61B 5/00* (2006.01)
*G06Q 50/22* (2012.01)

(52) U.S. Cl.
CPC ............ *G06F 19/36* (2013.01); *A61B 5/0002* (2013.01); *G06F 19/366* (2013.01); *A61B 5/0026* (2013.01); *G06F 19/322* (2013.01); *G06F 19/345* (2013.01); *G06F 19/3418* (2013.01); *G06Q 50/22* (2013.01)

(58) Field of Classification Search
None
See application file for complete search history.

(56) References Cited

U.S. PATENT DOCUMENTS 6,018,713 A    1/2000  Coli et al.
6,074,345 A    6/2000  Van Oostrom et al.
(Continued)

FOREIGN PATENT DOCUMENTS

| WO | 03015838 A2 | 2/2003 |
| WO | 2008026980 A1 | 3/2008 |
| WO | 2010035165 A2 | 4/2010 |

OTHER PUBLICATIONS

Zafena AB, International Application No. PCT/SE2011/051023, International Search Report, Dec. 28, 2011.

*Primary Examiner* — Mohamed Barakat
(74) *Attorney, Agent, or Firm* — Michael G. Johnston; Moore & Van Allen PLLC

(57) ABSTRACT

A system for enabling test data resulting from an analytic determination carried out on a clinical analytic device (20-1) to be communicated to an electronic patient information management system (80), the system comprising: a computer module (120-1) communicatively connectable to the clinical analytic device (20-1), a user operable control unit (140) communicatively connectable to the computer module (120-1), and an instrument tag (22-1) readable by the user operable control unit (140) and associated with the clinical analytic device (20-1).

25 Claims, 4 Drawing Sheets

(56) References Cited

U.S. PATENT DOCUMENTS

| | | |
|---|---|---|
| 8,050,938 B1* | 11/2011 | Green, Jr. .............. G06Q 50/22 |
| | | 705/2 |
| 2002/0082870 A1 | 6/2002 | Penny et al. |
| 2002/0178126 A1* | 11/2002 | Beck .................... A61B 5/0002 |
| | | 705/75 |
| 2002/0196141 A1 | 12/2002 | Boone et al. |
| 2003/0109904 A1 | 6/2003 | Silver et al. |
| 2004/0176913 A1 | 9/2004 | Kawatahara et al. |
| 2005/0108057 A1* | 5/2005 | Cohen ................. G06F 19/3468 |
| | | 705/3 |
| 2007/0150311 A1 | 6/2007 | Lazerus |
| 2008/0103377 A1 | 5/2008 | Brown |
| 2008/0217407 A1 | 9/2008 | Ackermann et al. |
| 2009/0163832 A1* | 6/2009 | Sunderani ........... G06F 19/3406 |
| | | 600/573 |

* cited by examiner

SYSTEM FOR ENABLING TEST DATA FROM A CLINICAL ANALYTIC DEVICE TO BE COMMUNICATED TO AN ELECTRONIC PATIENT INFORMATION MANAGEMENT SYSTEM

TECHNICAL FIELD

The present disclosure relates generally to solutions for enabling test data resulting from an analytic determination carried out on a clinical analytic device to be communicated to an electronic patient information management system.

TECHNICAL BACKGROUND

Point-of-care (POC) testing, also known as near-patient testing (NPT), refers to medical analytic testing of patient specimens at or near the location of patient care, including such testing in the immediate vicinity of the patients, so called bedside testing. POC testing can replace conventional centralized laboratory analysis by using distributed easy-to-operate POC devices, which may be operated by non-laboratory persons and in non-laboratory environments. Such devices constitute a new device class, POC analytic devices.

Advantages with clinical POC testing include; reduced risk of pre-analytical errors due to the immediateness of the analysis, the non-necessity of anticoagulation and reduced risk of erroneous labeling. In addition the immediate availability of analytical results, including the greater patient involvement, can increase the quality the patients experience in the contact with the health care organization, and improved treatment, including more rapid implementation of medical treatment. POC testing also makes the use of health care premises and personnel more efficient.

During the past decades there has been a considerable increase in the numbers of clinical POC devices in use at health facilities, but many of the devices are incapable of communicating with electronic patient information management systems. Electronic patient information management systems are also referred to as "laboratory information systems", LIS, or "health care information systems", HIS. During the same time period, there has been an increased desire towards increased use of electronic patient information management systems. Hence, there is an increased desire to transfer results from POC devices to such systems, for several reasons.

Many POC analytic devices in use are designed to present the results to the user on a display, and to print the results using a dedicated printer. The result therefore needs to be transcribed and entered manually, by keyboard, when storage of the result in electronic patient information management system is required. In connection with the transcription of an analytical result, the identity of the sample, or the patient, also needs to be transcribed into the patient information system. One example of this type of conventional POC analytic device is the present applicant's product Simple Simon® PT, which analyses blood samples and determines prothrombin time (PT).

With clinical analytic devices, where the patient identity is not directly connected with the analytical result, there is a risk that the connection between the result and the patient identity is lost, or confused with another patient's identity, before entering both into the electronic information management system. Also, the result may be erroneously transcribed. In fact, it has turned out that a significant percentage of results from POC testing that have been communicated to patients at the POC are not the same as the results that actually become entered into the electronic patient information management system. This has been revealed when patients later have been formally communicated the test result, e.g. by letter.

Another problem is traceability, i.e. which POC analytic device individual has been used in a test etc, which thus requires identity of the POC analytic devices to be stored as well. Such requirement adds an additional burden when also the device identity has to be transcribed, and as a result the entered identity is in practice often connected with errors, or is neglected. One solution to these problems is to replace the presently used POC devices with upgraded devices which will perform the desired tasks. The upgraded versions e.g. would 1) allow the identity of the sample or patient to be entered into its computer memory, 2) have the analytical result entered into its computer memory, 3) link the sample, or patient, identity to the analytical result, and 4) communicate the linked data, by use of the necessary communications protocol, to an electronic patient information management system.

Several POC analytic devices come in two models, one, still the more common, not adapted for connectivity to an electronic patient information management system, and another, upgraded version, adapted for use with such systems. For example HemoCue® models Hb 201+ and Hb 201 DM, where the former stores results which can be printed directly via an external printer or downloaded to a PC, while the latter can be made to also prompt the operator for supplementary data, i.e. patient identification and other information, and to transmit the complete data set, including, of course, the test result, to an electronic information system. Other such duos, one model non-connectable the other upgraded to connectivity, are: Orion's Quick Read 101 CRP (connectable only with accessory) and Quick Read Go, EKF's Hemocontrol and Hemocontrol Manager, Bodi's i-Chroma CRP and i-Chroma Duo, Vital's MicroSed R and Exite 20 and Macherey-Nagel's Uryxxon Relax and Uryxxon 500.

SUMMARY OF THE INVENTION

The applicant has found out that the existing solution of replacing existing POC analytic device models with new models that are fully compatible with the requirements for use with electronic patient information management systems is typically too costly. Such upgrading of analytical devices is often fully implemented and in use at centralized hospital laboratories, but not at many POC sites, especially not the smaller ones. One reason is that each new model of analytical device, regardless whether it is a POC device or a centralized laboratory device, is costly to develop, both in regard to hardware and software. There are new certification procedures to fulfill etc. In a centralized laboratory, a large number of tests are performed on each device, and the costs of a new device model will be dispersed on a large number of tests. This is not the case at a POC facility, particularly not at the smaller ones. At POC facilities, the number of tests performed on a given POC device is small and the cost of a device upgrade can only be dispersed on this small number, hence, device upgrade becomes a big economic issue. At a POC facility, upgrades of devices will tend to be postponed for years and years. In addition there is an educational problem, and, as with the problem of upgrade economics, this problem is also exasperated at POC sites, especially the smaller ones. At a POC site, the number of operators engaged in a given type of analysis is equally large as at centralized laboratory, but the test volume is much smaller. The POC site operators will spend less time performing a given test than the operators at a centralized laboratory, and hence, the educational effort to instigate a given upgrade at a POC site will be greater than at a centralized laboratory. There are several reasons for increased reluctance to upgrade devices, and instigate organizational changes, at a POC site than at a centralized laboratory. Still, and in particular at POC test sites, there is an unfulfilled desire to avoid manual transfers of data into electronic patient information management systems. Importantly, the applicant is aware that many, most, or even all, of the existing, non-upgraded, POC analytic testing devices support some output data protocol for electronic delivery of data comprising test data, although not intended for communication nor compatible with an electronic patient information management system, but with e.g. a printer. The Simple Simon® PT has a USB interface from which it is possible to electronically obtain test data.

Many existing POC analytic devices more or less dump test data on the port, e.g. a printer or serial port, without any other additional information, such as identification of the instrument, and often it is not possible to e.g. request or control the data output via the port.

Hence, in view of the above, one object of this disclosure is to present a solution overcoming, or at least alleviating, problems in the prior art.

A more specific object is to present a solution that enables test data resulting from an analytic determination carried out on a clinical analytic device to be communicated to an electronic patient information management system. An even more specific object is to accomplish such a solution that is compatible with virtually any existing clinical analytic devices, including for example the present applicants POC analytic device Simple Simon® PT, that are already supporting some output data protocol for delivery of data comprising test data.

The invention is defined by the appended independent claims. Preferred embodiments are set forth in the dependent claims and in the following description and drawings.

Hence, the above-mentioned and other objects and advantages, which will be evident from the following description, are:

According to a first aspect achieved by a system for enabling test data resulting from an analytic determination carried out on a clinical analytic device to be communicated, together with any required supplementary data, to an electronic patient information management system. The system comprises a computer module communicatively connectable to the clinical analytic device, a user operable control unit communicatively connectable to the computer module, and an instrument tag, associated with the clinical analytic device, readable by the user operable control unit. The user operable control unit comprises a tag reader for selecting the clinical analytic device by reading the instrument tag and is arranged to, in response to a reading of the instrument tag, cause a module activating signal and/or mode selecting signal to be transmitted to the computer module. The computer module is arranged to receive the module activating signal and/or mode selecting signal and in response identify test data in received data from the clinical analytic device, wherein the identification of the test data is carried out according to a selected operative mode of the computer module, the selected operative mode being associated with the output data protocol of the clinical analytic device.

Hence, the system enables the test data to be identified and be available in the computer module, which can be understood as a pre-requisite for being able to further arrange the test data for compatibility with and communication to the electronic patient information management system.

The instrument tag in combination with the control unit and tag reader allows a user to read the tag and thereby inform the computer module that the clinical analytic device associated with the instrument tag is expected to deliver test data, whereby the computer module can respond to this and identify the test data according to an operative mode selected for this purpose. It should be understood that this makes the solution compatible with virtually any existing clinical analytic devices that is supporting some output data protocol for delivery of data comprising test data.

Typically there may be several clinical analytic device types supported by the computer module and the selected mode thus be selected from multiple predetermined operative modes available to the computer module, but it is also possible with only one clinical analytic device supported by the computer module and the selected mode can then be predetermined.

Further advantages include that the system allows user interaction in the same manner independent on which clinical analytic device or devices are operated with the system. Adding support in the system for another instrument may simply be a matter of adding an operative mode in the computer module, for example by updating software of the computer module, and adding an instrument tag associated with the added operative mode and the instrument in question. The tag reading also simplifies user input and reduces the risk of human introduced errors. The present solution is thus also flexible, scalable and user friendly.

The present solution is generally applicable to clinical analytic devices and only one type of comparatively inexpensive upgrade, and one type of educational effort, may suffice to upgrade most, perhaps all, clinical analytical devices at a POC facility. The present invention enables surmounting several difficulties associated with the unfulfilled desire at POC test sites to eradicate manual transcription of clinical analytical data and sample identity information etc—no more keyboards. The solution will contribute to the instigation of improved routines that will improve medical care by increased efficiency and quality of clinical testing and analysis.

According to a second aspect achieved by a computer module as claimed in claims 2-11.

According to a third aspect achieved by a user operable control unit, as claimed in claims 12-16, communicatively connectable to the computer module.

According to a fourth aspect achieved by an instrument tag, as claimed in claim 17, associated with a clinical analytic device to which the computer module is communicatively connectable and that is readable by the user operable control unit.

According to a fifth aspect achieved by a hub unit to which multiple computer modules and the user operable control unit are connectable.

According to a sixth aspect achieved by a system, comprising the computer module and one or more of the following: the control unit, the instrument tag, the hub unit.

According to a seventh aspect achieved by a method of operating the computer module.

According to an eight aspect achieved by a computer program product loadable into a memory of the computer module and comprising program code adapted for causing the computer module to performing the steps according to the method.

By two entities being communicatively connectable is meant that a direct or indirect connection can be established between the entities and through which at least one of the entities can cause information to be directly or indirectly transmitted to the other entity.

By clinical analytic device output data protocol is meant data protocol according to which a clinical analytic device arranges its output data. That is, how the received data from the clinical analytic device module will be arranged.

By computer module operatively compatible with a clinical analytic device is meant that the computer module can identify test data in received data from the clinical analytic device.

Status, in the context of the claims, may for example indicate whether the data is considered valid or not according to a test criterion, for example using a checksum or comparing to an expected format or range.

BRIEF DESCRIPTION OF THE DRAWINGS

The above, as well as other aspects, objects and advantages of the present invention, will be better understood through the following illustrative and non-limited detailed description, with reference to the appended schematic drawings.

FIG. 3 schematically shows steps of an exemplary method that a user operable control unit according to one embodiment can be operated in accordance with.

FIG. 4 schematically shows steps of an exemplary method of how a user interface in one embodiment can be operated in accordance with.

In the drawings the same reference numerals are used for same, similar or corresponding features, even when the reference numerals refer to features in different embodiments.

DETAILED DESCRIPTION

Figure 1:
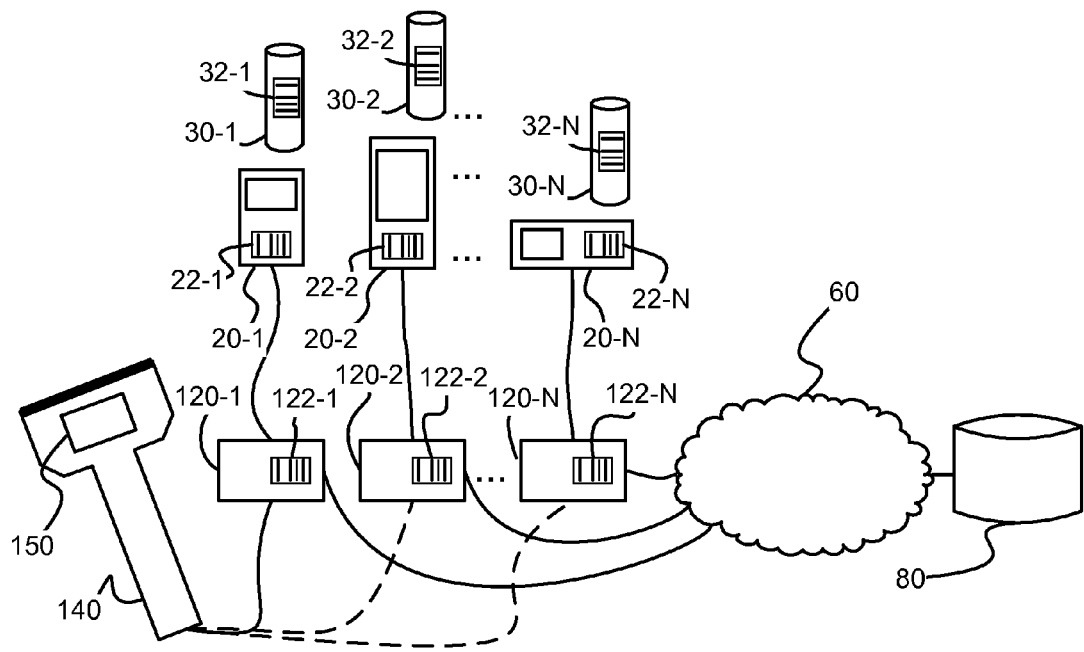
FIG. 1 is a schematic view of a first exemplary system.

FIG. 1 is a schematic view of a first exemplary system. The system may comprise one or more computer modules 120-1 . . . 120-N and a user operable control unit 140 communicatively connectable to the computer modules 120-1 . . . 120-N. In other embodiments there may be more than one user operable control unit, each communicatively connectable to a respective one or more, preferably all, of the computer modules 120-1 . . . 120-N. Each computer module 120-1 . . . 120-N may be communicatively connected to only one clinical analytic device 20-1 . . . 20-N, so that it is possible for the control unit 140 to indirectly address each clinical analytic device 20-1 . . . 20-N via the respective computer module. There is a respective instrument tag 22-1 . . . 22-N associated with the clinical analytic devices 20-1 . . . 20-N, and a respective computer module tag 122-1 . . . 122-N associated with the computer modules 120-1 . . . 120-N. As shown, the tags 22-1 . . . 22-N, 120-1 . . . 120-N may be attached to the respective module or device. The shown system further comprises a user interface 150, here connected to, and integrated with the control unit 140. The user interface 150 may be a high resolution screen, may be a touch screen, but can also be a small low resolution and low cost LCD. In one embodiment the user interface 150 may simply be based on light emitting diodes, each connected to a pre-printed text, and communicating through change of the emitted light, such as different colors and/or switching and/or pulsating the emitted light. It is also possible with user interfaces 150 that are not, or not only, visually interacting with the user, instead for example by audio or sense, such as through vibrations. Note that, as will be further discussed below, the user interface 150 can be connected to and/or integrated with also other parts of the system than the control unit 140. For example, there may be a separate user interface unit, for example a screen, communicatively connectable to each one of the computer modules 120-1 . . . 120-N, or there may be multiple such units so that each computer module 120-1 . . . 120-N can be connected to one user interface unit 150, possibly be integrated with such unit.

In FIG. 1 the control unit 140 is shown connected by wire, which for example may be a USB cable, to one of the computer modules, but can be connected to any other of the computer modules by moving and connecting the wire to that module instead. Each of the 120-1 . . . 120-N is communicatively connectable to a respective one of clinical analytic devices 20-1 . . . 20-N. The clinical analytic devices 20-1 . . . 20-N may be of same or different type and/or model. The computer modules 120-1 . . . 120-N are shown connected to the clinical analytic devices 20-1 . . . 20-N by wire, for example a serial cable, connected to a clinical analytic device data output port, for example a printer port, and a port of the computer module 120-1 . . . 120-N, for example a USB port. There may be an adapter (not shown) for connection at one or both ends at any one of the cables if the cable is else not directly compatible with a clinical analytic device data output port and/or a port of the computer module 120-1 . . . 120-N. For example, when the computer module port is an USB port, the wire is a USB cable, and the clinical analytic device port is a RS-232 port, a RS-232 to USB adapter may be used.

The clinical analytic devices 20-1 . . . 20-N shown are able to carry out an analytic determination on a respective sample 30-1 . . . 30-N of a type which the clinical analytic device 20-1 . . . 20-N is designed to analyze, and provide data that comprises test data resulting from the analytic determination on the data output port. To each of the samples 30-1 . . . 30-N shown there is associated a supplementary data tag 32-1 . . . 32-N comprising or linking to supplementary data associated with the respective sample. Such supplementary data may for example be test identity data, such as patient identity data and/or sample identity data.

The instrument tags 22-1 . . . 22-N comprises information connected to the output data protocol of the clinical analytic devices 20-1 . . . 20-N and/or the identity of the respective clinical analytical device 20-1, and may also comprise information connected to the data protocol of the electronic patient information management system 80. The type of instrument is one example of information connected to the output data protocol of the clinical analytic device 20-1. The instrument tag 22-1 may also comprise information enabling automatic identification of the type of tag, that is, that it is an instrument tag, which may be used for correctly interpreting rest of the information encoded in the tag.

For example, an instrument may encode the following information "LMC-ZAF1-1234", where "LMC-" is information for identifying that the tag is an instrument tag, "ZAF1-" identifies the type of instrument, and "1234" uniquely identifies the device individual.

The computer module tags 122-1 . . . 122-N comprise information of the identity of the respective computer module 120-1 . . . 120-N, and may also comprise information connected to the data protocol of the electronic patient information management system 80.

The user operable control unit 140 shown is arranged to be handheld, and is shaped as and comprises an optical reader, here a bar code reader, so that it is able to read the tags 22-1 . . . 22-N, 122-1 . . . 122-N and 32-1 . . . 32-N. The control unit 140 is preferably arranged to be movable by a user operating it, so it for example can be moved to different clinical analytic devices 20-1 . . . 20-N and/or computer modules 120-1 . . . 120-N at a location, such as in order to read tags 22-1 . . . 22-N, 122-1 . . . 122-N and/or 32-1 . . . 32-N, that is, the control unit 140 may be arranged to be mobile, at least locally. Other examples of optical readers are 2-dimensional optical code readers or camera based readers. The optical reader is one example of a tag reader. Another example of a tag reader is a RFID-reader. The tag reader is one example of means for selecting a clinical analytic device to be used for carrying out an analytical determination since it can be used to read the tags 22-1 . . . 22-N. In other embodiments means for selecting a clinical analytic device 20-1 can be a user interface 150 of the control unit 140 through which a user identifies the clinical analytic device 20-1 by selection from a list or similar, which list may be updated in response to that a new clinical analytic device and respective computer module is changed, for example added or removed from the system, or connected/disconnected from each other. The tags 22-1 . . . 22-N, 122-1 . . . 122-N and 32-1 . . . 32-N are readable by the control unit 140, that is, the design of the tags and the tag reader should be compatible so that the reader can read the tags. In the shown example the tags are bar codes.

Typically the tag reader reads information directly from a tag 22-1 . . . 22-N, and/or 122-1 . . . 122-N and/or 32-1 . . . 32-N. However, it is also possible that some or all tags instead of comprising certain information, link to that information, and that the tag reader, or any device the tag reader is communicatively connected to, instead fetches the information via the link.

Each of the 120-1 . . . 120-N shown in FIG. 1 are communicatively connected to a network 60, through which an electronic patient information management system 80 is accessible. The connection may be by wire as shown, for example a network cable, such as an Ethernet cable, from a network port of the respective one of the computer modules 120-1 . . . 120-N to a network port of e.g. a Local Area Network (LAN) port or hub at the facility where the system is located and that provide access to the network 60. In other embodiments one or more of the computer modules 120-1 . . . 120-N may be wirelessly connectable to the network 40, such through a Wireless LAN (WLAN).

Figure 2:
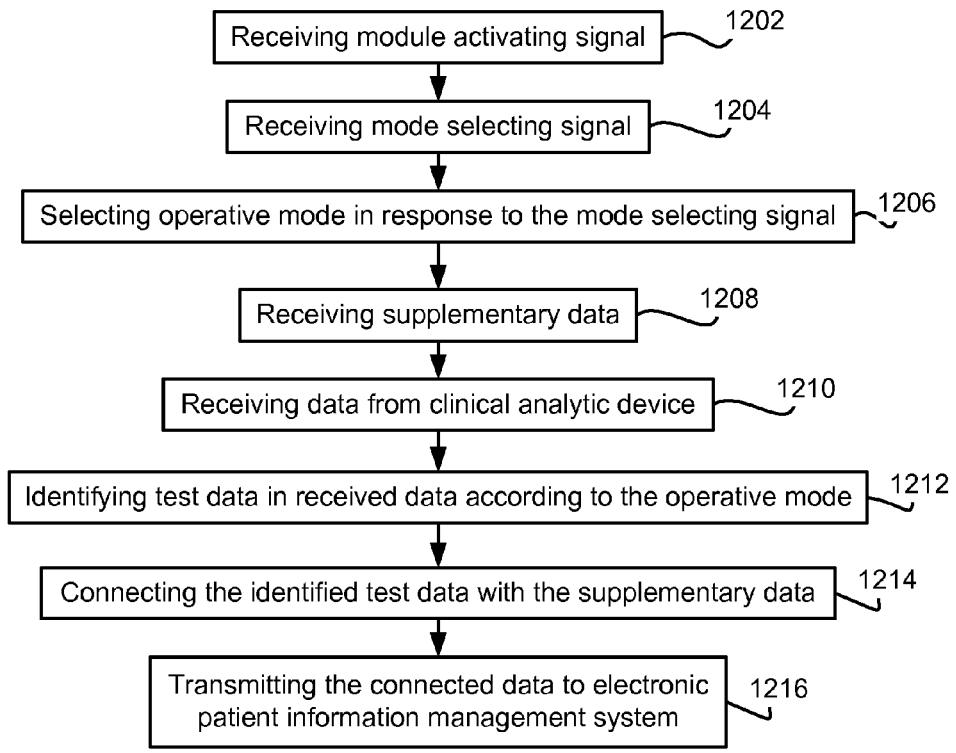
FIG. 2 schematically shows steps of an exemplary method that a computer module according to one embodiment can be arranged to carry out.

FIG. 2 schematically shows steps of an exemplary method that a computer module according to one embodiment can be arranged to carry out, and will now be used with reference to the system discussed above to further explain and discuss the solution according to the present disclosure, focusing on one of the computer modules 120-1, connected to the clinical analytic device 20-1.

In a step 1202 a module activating signal is received, preferably transmitted to the computer module 120-1 by use of the control unit 140, typically by using the control unit 140 to read the instrument tag 22-1 and/or the computer module tag 122-1. The module activating signal may comprise information connected to the identity of the computer module and/or the identity of the clinical analytical device, and may comprise information read from said tags 22-1 and/or 122-1.

In a step 1204 a mode selecting signal is received, preferably transmitted to the computer module 120-1 by use of the control unit 140, typically by using the control unit 140 to read the instrument tag 22-1 and/or the computer module tag 122-1. The mode selecting signal comprises information connected to the output data protocol of the clinical analytic device and may comprise information read from said tags 22-1 and/or 122-1. The type and/or identity of the clinical analytic device may be information connected to the output data protocol of the clinical analytic device 20-1 if, for example, the computer module 120-1 has stored information that said type and/or identity deliver data according to a certain data protocol. Hence, also the identity of the computer module 120-1 may be information connected to the output data protocol of the clinical analytic device 20-1 if, for example, the computer module 120-1 has stored the identity and/or type of the clinical analytical device 20-1 to which it is connected. Such relation, or pairing of the computer module 120-1 to the clinical analytic device 20-1, may be established and stored in connection with that the computer module 120-1 is being connected to the clinical analytic device 20-1, for example in response to that having the control unit 140 to read both the instrument tag 22-1 and the computer module tag 122-1.

The module activating signal and the mode selecting signal may be one and the same signal.

Still referring to FIG. 2, in a step 1206, an operative mode of the computer module 120-1 is being selected in response to the mode selecting signal. The operative mode may be selected from multiple predetermined operative modes of the computer module 120-1, each one associated with a respective clinical analytic device output data protocol. The multiple predetermined operative modes may be stored in a memory of the computer module 120-1 and may for example be realized by program code enabling the computer module 120-1 to interpret data received from different clinical analytic devices 20-1 . . . 20-N and identify test data in received data from these devices.

In another embodiment the mode may be selected and stored in a memory of the computer module 120-1 so that there is no need to select the mode every time the clinical analytic device 20-1 deliver test data, that is, corresponding steps 1204 and 1206 in FIG. 2, may be omitted and executed separately.

In a step 1208, supplementary data is received, preferably from the control unit 140 and typically by using the control unit to read the supplementary data tag 32-1. In other embodiments, the supplementary data may be received indirectly from the control unit 140, for example, the control unit 140 may be used to read a tag linking to the supplementary data, the link is sent to the computer module 120-1, or any other entity communicatively connected to the computer module 120-1, which in turn fetches the supplementary data using the link and when needed transmits the supplementary data to the computer module 120-1.

In a step 1210, data is received from the clinical analytic device 20-1, and in step 1212 the test data is being identified in the received data according to the selected operative mode.

In a step 1214, the identified test data is connected and arranged with the supplementary data according to a data protocol of the electronic patient information management system 80, which may be selected in response to a second mode selecting signal transmitted by use of the control unit 140, that is, in a similar manner as discussed regarding the previously mentioned mode selecting signal. The second mode selecting signal thus preferably comprises information connected to the data protocol of the electronic patient information management system 80, and may result from using the control unit 140 to read the instrument tag 22-1 and/or the computer module tag 122-1, or another tag, connected to such information. The selection may be made from many predetermined data protocols of electronic patient information management systems. Selection of the data protocol of the electronic patient information management system 80 typically only has to be made once per computer module and location, such as the first time the computer module is installed at the location.

In a step 1216, the connected and arranged data is transmitted to the electronic patient information management system 80. Step 1214 is typically executed by a processor and step 1216 by a transmitter, which may be the processor (not shown) of the computer module 120-1 and a transmitter (not shown) of the computer module 120-1.

Figure 3:
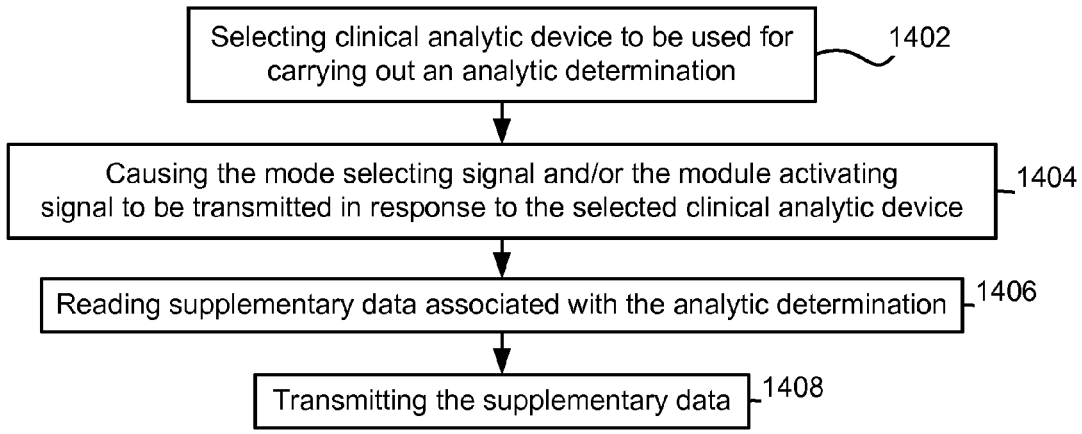

FIG. 3 schematically shows steps of an exemplary method that a user operable control unit 140 according to one embodiment can be operated in accordance with, and will now be used with reference to the above to further explain and discuss the solution according to the present disclosure, focusing on the control unit 140. In a step 1402 a user operates the control unit 140 to select a clinical analytic device 20-1 to be used for carrying out an analytic determination. In response thereto, in a step 1404, the control unit 140 is causing the module activating signal and/or the mode selecting signal to be transmitted to the computer module 120-1. More details on how this can be accomplished have been discussed above. In a step 1406 the control unit 140 is used to read supplementary data associated with the analytic determination. More details on how this can be accomplished have been discussed above. In some embodiments there may be supplementary data to be read from different sources, for example tags, and there may then be multiple instances of step 1406, such as one per source. Then, in a step 1408, the supplementary data is being transmitted, for example to the control unit 140. More details on how this can be accomplished have been discussed above.

Figure 4:
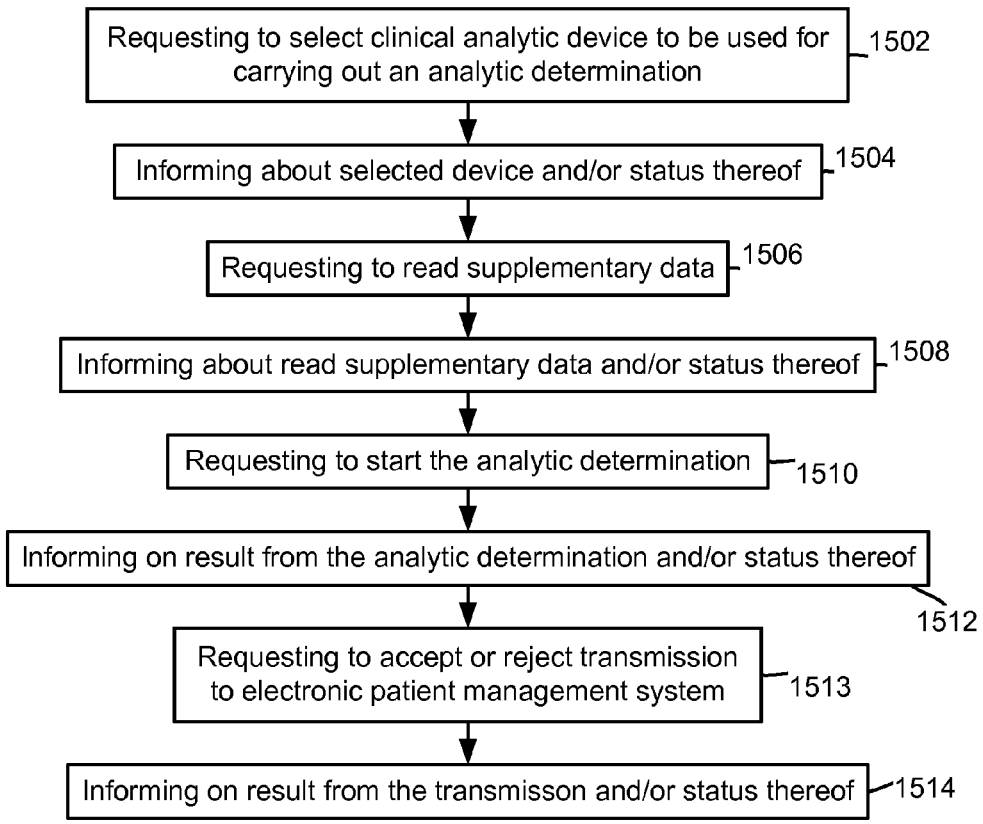

FIG. 4 schematically shows steps of an exemplary method according to which a user interface 150 can be controlled to operate, and will now be used with reference to the above to further explain and discuss the solution according to the present disclosure. A controller of the user interface 150 may be located in any entity to which the user interface 150 is communicatively connected to, for example, in case of a user interface 150 communicatively connected to a computer module 120-1, the processor of the computer module 120-1 preferably is arranged to control the user interface 150.

In a step 1502, the user interface 150 is controlled to request a user to select a clinical analytic device 20-1 to be used for carrying out an analytic determination. In response to this it is then for example expected that the control unit 140 is used, for example according to what has been discussed above.

Then, in a step 1504, the user interface 150 is controlled to inform on the result from step 1502, that is, what has been registered by the use of the control unit 140, which for example may be the identity of the device 20-1, that is, so that the user can check that the intended device actually has been registered, and/or the user interface 150 is controlled to inform on the status of what has been registered. Status can for example result from that a check is made on whether what has been registered is considered valid or not according to a test criterion, for example using a checksum or comparing to an expected format or range, which may be predetermined. Such checks can be performed by the controller of the user interface 150 and/or by any other entity communicatively connected to the controller.

In a step 1506, the user interface 150 is controlled to request a user to read supplementary data. In response to this it is then for example expected that the control unit 140 is used, for example according to what has been discussed above.

In a step 1508, the user interface 150 is controlled to inform about the result from step 1506, that is, what supplementary data actually have been read and registered, by the use of the control unit 140 and/or the user interface 150 is controlled to inform on the status of this. Step 1508 may thus correspond to step 1504 but is in regard of read supplementary instead of what has been registered regarding selected clinical analytic device 20-1.

In a step 1510, the user interface 150 is controlled to request a user to start the analytic determination. In response to this it is then for example expected that the user operates the clinical analytic device 20-1 previously selected, for example by inserting a sample and pressing a start button, possibly followed by pressing a print button or similar if this is needed to make the clinical analytic device 20-1 to output data comprising test data from the analytic determination to the port to which the computer module 120-1 is connected.

In a step 1512, the user interface 150 is controlled to inform on the result from step 1510, that is, the result from the analytic determination, typically the test data, and/or what has been registered as test data by the computer module 120-1, and/or the user interface 150 is controlled to inform on the status of this. Step 1512 may thus similar to step 1504 and 1508 but in regard of the result from the analytic determination.

In a step 1513, the user interface 150 is controlled to request the user to accept or reject transmission of test data and/or supplementary data to the electronic patient information management system 80, which allows for a last check. In connection with this step, or before, there may be another step (not shown) where the user is requested to input user identity data, for example by use of the control unit 140 and a tag associated with the user identity in a similar manner as for supplementary data discussed in the foregoing. The user identity data may be considered to be supplementary data and/or valid input of user identity may be considered as acceptance following the request. In connection with step 1513, preferably before, whether all supplementary data that is expected or needed according to a predetermined criterion is available, so that the user interface 150 can be controlled to inform a user that something is missing and it can be made sure that no incomplete data is transmitted to the electronic patient information management system 80. This check may be performed by the controller of the user interface 150 or by the entity arranged to perform the previously discussed step 1214 and/or step 1215.

In a step 1514, the user interface 150 is controlled to inform about the result from step 1513, that is, the result from the transmission, for example by referring the user to make a check on a PC connected to and able to display what is registered in the electronic patient information management system 80, or if the entity in control of the user interface 150 has the ability, the user interface 150 can be controlled to display this data itself, and/or the user interface 150 is controlled to inform on the status of what has been registered, for example, the electronic patient information management system 80 may perform some check itself and send back status information.

In other embodiments, some or all of applicable above mentioned steps, such as steps 1502-1514, may be omitted, may be in different order or may be combined. For example: One or many of the requesting steps may be omitted, for example if considered implicit to a user, such as step 1502 and/or step 1510. One or many of the informing steps may be omitted, or combined, so that the user is informed in a single step, which e.g. may be in connection with the accept/reject step 1513. The step of requesting to read supplementary data may be located after requesting to start the analytic determination in step 1510 or after step 1512. The step 1504 may be combined with step 1510. The step 1512 may be omitted, for example if it is expected that a user checks the result directly on a display of the clinical analytic device 20-1.

Now some other exemplary systems will be discussed to further illustrate variations and different aspects of the present solution. Focus will be on differences compared to what has already been disclosed and features that can be the same as already discussed may therefore be omitted in the following. It will logically follow, or the skilled person will recognize, which of the features already discussed are compatible and/or can be combined with the exemplary systems and features discussed below.

Figure 5:
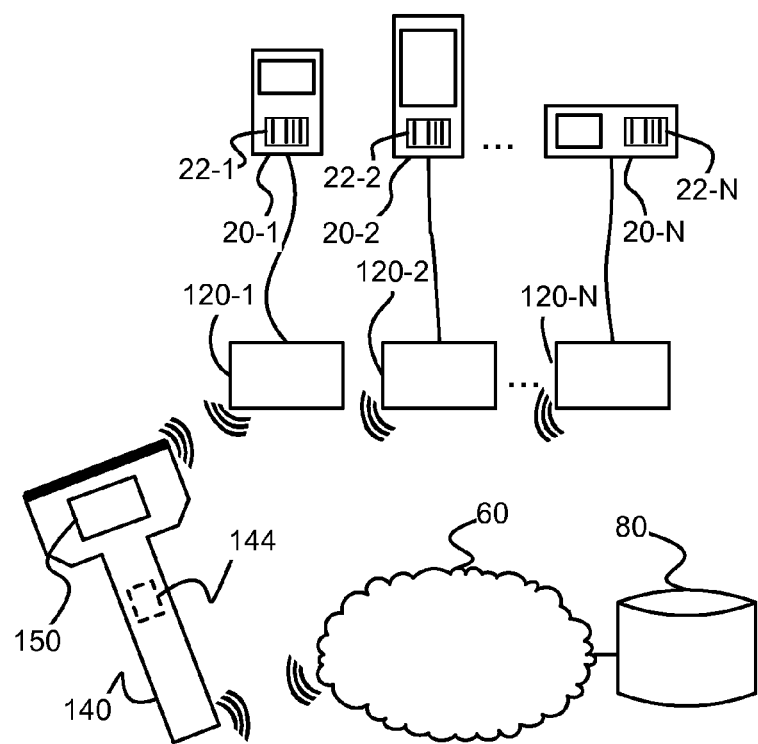
FIG. 5 is a schematic view of a second exemplary system.

FIG. 5 is a schematic view of a second exemplary system. Here the control unit 140 is communicatively connected to the network 60 instead of the computer modules 120-1 . . . 120-N. The control unit 140 may comprise a transmitter (not shown), which is arranged to execute the previously discussed step 1216. The control unit 140 may also comprise a processor 144, arranged to execute the previously discussed step 1214. When there is user interface 150 integrated with the control unit 140, the control unit 140, or the processor 144, may be used to control the user interface 150. In another embodiment, the processor (not shown) of respective computer module 120- . . . 120-N may be arranged to execute step 1214, and the respective computer module 120- . . . 120-N may be arranged to transmit the connected data to the control unit 140, which in turn is arranged to execute step 1216. The control unit 140 is connected wirelessly to the computer modules 120-1 . . . 120-N and to the network 60. For example, it may be connected by use of Bluetooth® to the computer modules and via a WLAN to the network 60, but also other wireless type of connections may be used. In other embodiments, the same kind of wireless connection may be used to both the computer modules 120-1 . . . 120-N and to the network 60, or one of these connections may be by wire. Wireless connections are often considered less secure and there may be reluctance to send test results connected to patients over such connections. This may be solved by encrypting the traffic sent over such connections or by making sure that direct patient related information is never sent together with test data over such connections. For example, when the control unit 140 is arranged to execute step 1214 and comprises the user interface 150, supplementary data comprising information related to patient identity is not needed to be transmitted over a wireless connection to the computer modules 120- . . . 120-N.

Figure 6:
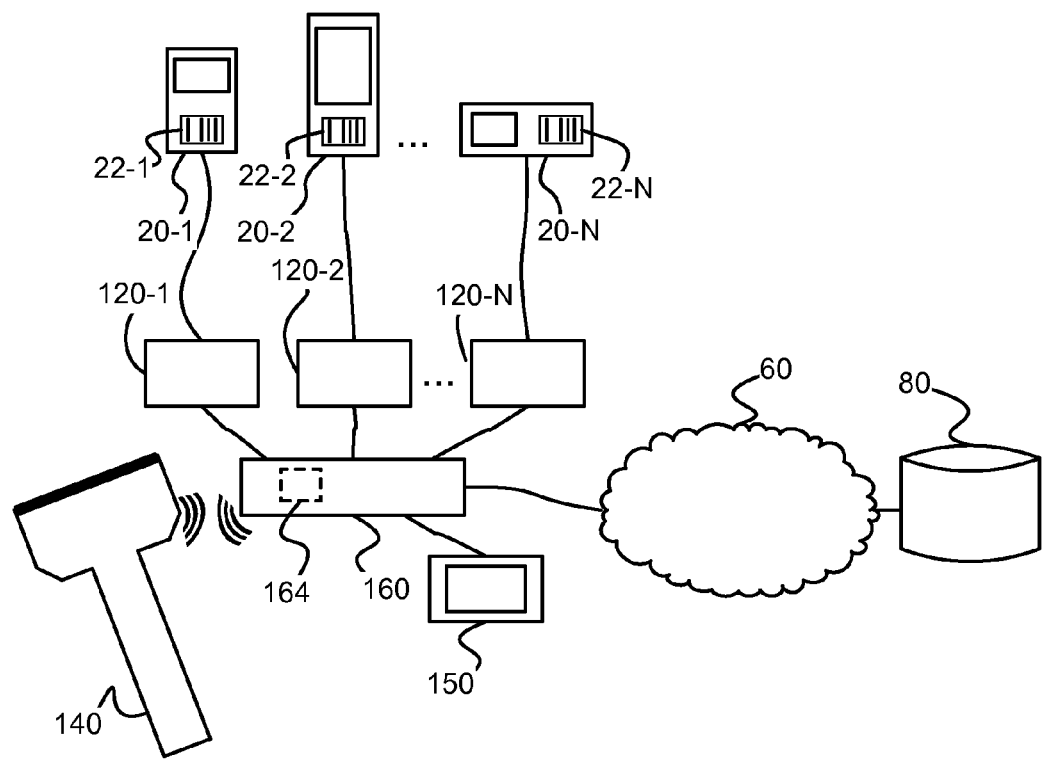
FIG. 6 is a schematic view of a third exemplary system.

FIG. 6 is a schematic view of a third exemplary system. Here the system comprises a hub unit 160, to which the control unit 140 and the computer modules 120-1 . . . 120-N are communicatively connected, and through which the control unit 140 and the computer modules 120-1 . . . 120-N are communicatively connected to each other. A separate user interface 150, here a screen, is communicatively connected to the hub unit 160. All shown connections to the hub unit 160 are by wire, except with the control unit 140 which is shown wirelessly connected. In other embodiments one or more of the shown wired connections may be wireless instead, for example of types previously mentioned, and/or the connection with the control unit may be by wire. The hub unit 160 may comprise a transmitter (not shown), which is arranged to execute the previously discussed step 1216. The hub unit may also comprise a processor 164, arranged to execute the previously discussed step 1214. The hub unit, or the processor 164 of the hub unit, may be used to control the user interface 150. In another embodiment the processor (not shown) of the computer modules 120-1 . . . 120-N is arranged to execute step 1214 and the transmitter of the hub unit step is arranged to execute step 1216.

Figure 7:
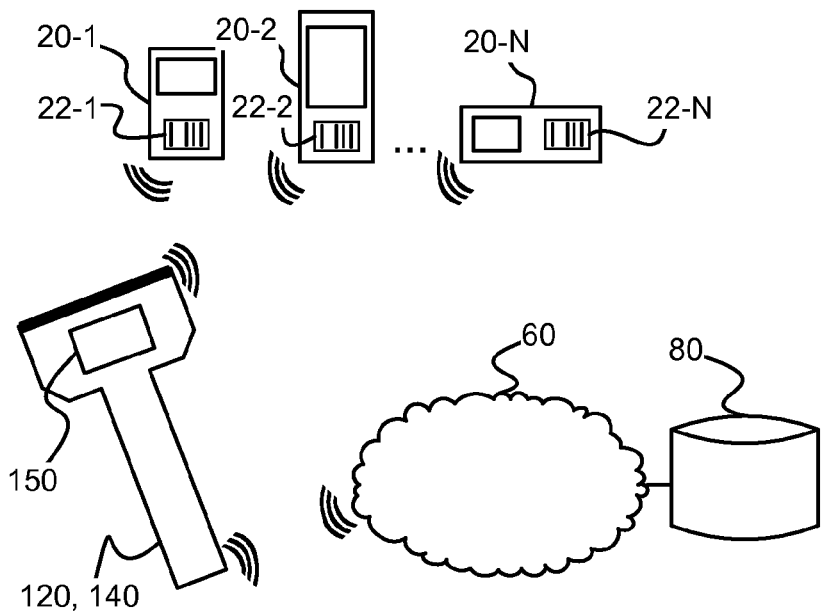
FIG. 7 is a schematic view of a fourth exemplary system.

FIG. 7 is a schematic view of a fourth exemplary system. Here the control unit 140 and a computer module 120 are combined, preferably integrated in a single unit 120, 140, together with a user interface 150. Preferably the combined unit is handheld, and may have a similar outer appearance as the control unit 140. In another embodiment the user interface is a separate entity. The combined unit 120, 140 is communicatively connected to the network 60 and to respective clinical analytic devices 20-1 . . . 20-N. Preferably these connections are wireless, provided that the clinical analytic devices 20-1 . . . 20-N support wireless provision of data comprising test data. In other embodiments the connection to the clinical analytic devices 20-1 . . . 20-N and/or to the network 60 may be by wire.

Figure 8:
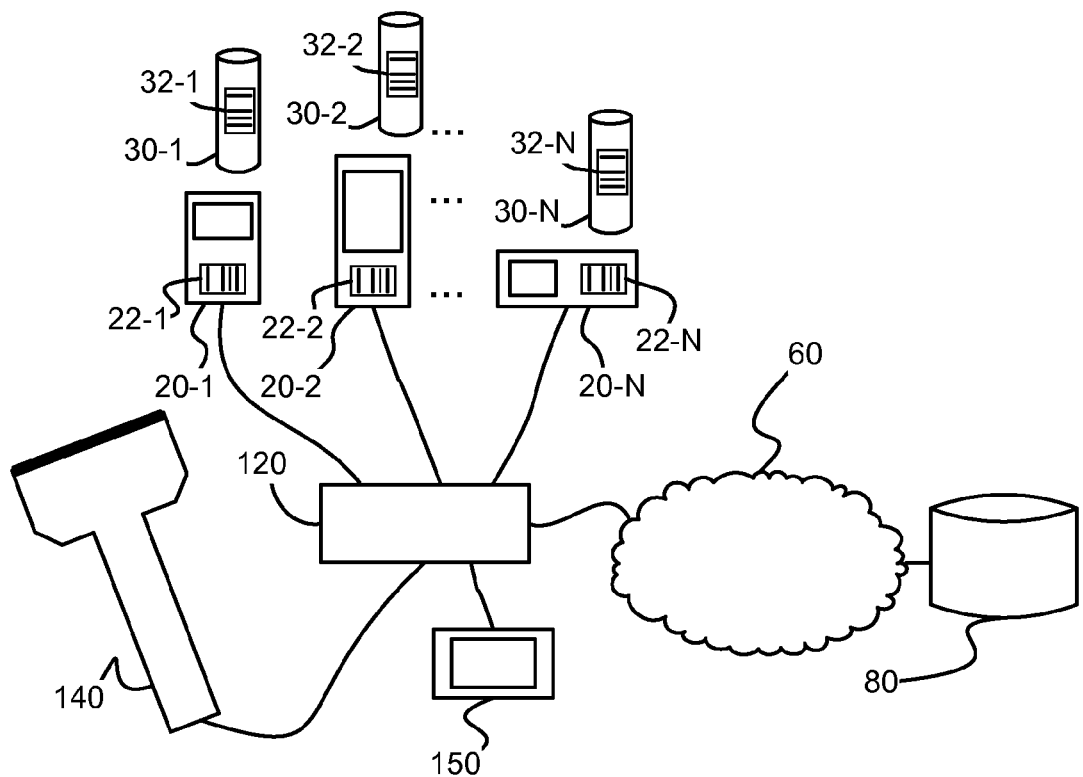
FIG. 8 is a schematic view of a fifth exemplary system.

FIG. 8 is a schematic view of a fifth exemplary system, where multiple clinical analytic devices 20-1 . . . 20-N, which as in previous examples may be same and/or of different types, are communicatively connected to a single computer module 120 by wire. The computer module 120 and the control unit 140 are here separate units also communicatively connected by wire. The control unit 140 may be a conventional tag reader, such as a bar code reader, connected to the computer module 120 by a USB cable. A separate user interface 150, here a screen, is communicatively connected to the computer module 120.

Some clinical analytical devices 20-1 . . . 20-N may be connected directly to ports of the computer module 120 while others, especially many present day devices that output data via a dedicated printer port, may require an adapter (not shown), e.g. a printer-port-to-usb dongle, in order to enable several connected clinical analytic devices 20-1 . . . 20-N to be communicatively connectable to the computer module 120 and be used in parallel, not only sequentially. Parallel use means that an analytic determination can be started on one of the clinical analytic devices 20-1 . . . 20-N when the computer module is still expecting data input, e.g. test data, from another of the clinical analytic devices 20-1 . . . 20-N, which perhaps is still analyzing a sample and not yet has been able to deliver any test data to the computer module 120. The adapter may add a unique identifier, which else may not be present in the output of the clinical data analytic device 20-1 . . . 20-N, making it possible for the computer module 120 to determine from which one of the devices 20-1 . . . 20-N in parallel use that received test data belongs to.

With some clinical analytical devices 20-1 . . . 20-N, the reading of the instrument tag 22-1 . . . 22-N may give rise to a mode selecting signal that will enable the computer module 120 to establish two-way communication with the clinical analytical device 20-1 . . . 20-N, but with many present day devices the only communication that can be established is one way, where the device only transmits data and the computer module 120 thus only receives data.

The exemplary system shown in FIG. 7 has a modular computer 120 integrated with the control unit 140, a modular computer 120 that can establish wireless communication with e.g. three clinical analytic devices 20-1 . . . 20-N. The system shown in FIG. 8 has similar functionality as that shown in FIG. 7, but in which all communication is by wire. Typically, it will be more straightforward to integrate a present day clinical analytical device having only a printer port for electronic output of data, into a system like that shown in FIG. 8 instead of one shown in FIG. 7.

The present invention enables automatic transfer of analytical data from a clinical analytic device 20-1 that only has a printer port, to an electronic patient information management system 80, and provides means of how such analytical data may be coupled to other, supplementary, data, as required by the management system 80, and transferred to the management system 80. Upon receipt of information from reading of the instrument tag 22-1, the computer module 120 may select a mode of operation that allows it to recognize and correctly interpret data received from the clinical analytic device 20-1, and, while operating in the selected mode, the computer module 120 may instruct the user what supplementary data is required to be input, for example by reading a supplementary data tag using the same tag reader as was used for reading the instrument tag 22-1, in order to full-fill the requirements of the electronic patient information management system 80, to which all the required data when complete, subsequently may be transmitted in a format as required by the electronic patient information management system 80.

In addition to being transferred to the electronic patient information management system 80, data may be stored in an electronic memory of the computer module 120 in order to provide traceability and documentation as desired by the health care organization using the system.

In some embodiments, corresponding steps 1214 and 1216, as discussed in the foregoing, may be arranged to be executed completely or partly by another entity than the computer module 120 or the control unit 140, said another entity being communicatively connectable to the computer module 120 and/or the control unit 140. Such entity may for example be the hub unit 160, or may be another, separate unit (not shown). In such embodiments, step 1408 is transmitting to the entity arranged to execute step 1214.

Power supply of the different entities discussed in the foregoing may be by wire from a power socket, by a wired connection to another of the entities that in turn is directly or indirectly power supplied, and/or by batteries. The latter is typically preferred for the control unit 140, especially when it is arranged to communicate wirelessly.

As implied by the name and is understood from the above description, the computer module 120 comprises a processor unit, memory etc. It may for example, at least in regard to the hardware, correspond to a commercially available computer, for example so called "nettop" computer, that is, a very small form factor, inexpensive, low-power desktop computer, such as an Asus Eee Box model or similar. It is also possible with other more or less powerful computer modules, and such that may comprise specially designed hardware. The software running on the computer module 120 is preferably specially designed software for carrying out the tasks of the computer module, and preferably dedicated to only carry out tasks relevant for the solution discussed herein and not allow, or at least restrict, the computer module 120 to be accessed and controlled by a user in any way that does not relate to the present solution. Preferably the software also does not allow, or at least does restrict, the computer module 120 to initiate any external communication that does not relate to or is required by the present solution. Such measures in the software provides for a high level of data protection and data safety.

Computer module tag or tags 122-1 . . . 122-N can be useful when the software of the computer module 120 is to be updated and/or configured, the reading of the computer module tag may select proper settings and communications protocol of e.g. the electronic patient information management system 80, for example by selecting a certain software to be installed or selecting a certain operative mode, e.g. one of many predetermined operative modes, of the software. The reading of the computer module tag may also instruct the computer module what supplementary data are needed for compatibility with the health care organization in which the system is functioning, that is, what supplementary data are required and/or usable with the electronic patient information management system 80 and/or the data protocol of the electronic patient information management system 80. Generally, use of a computer tag or tags facilitates adaptation, in particular of the computer module 120, to the milieu in which it is to function, in particular to the electronic patient information management system 80.

Any illustration and description in the drawings and in the foregoing description are to be considered exemplary and not restrictive. The invention is not limited to the disclosed embodiments.

The present invention is defined by the claims and variations to the disclosed embodiments can be understood and effected by the person skilled in the art in practicing the claimed invention, for example by studying the drawings, the disclosure, and the claims. Use of the word "comprising" in the claims does not exclude other elements or steps, and use of the article "a" or "an" does not exclude a plurality. Occurrence of features in different dependent claims does not per se exclude a combination of these features. Any reference signs in the claims are for increasing intelligibility and shall not be construed as limiting the scope of the claims.

The invention claimed is:

1. A system for enabling test data resulting from an analytic determination carried out on a clinical analytic device to be delivered to an electronic patient information management system, the system comprising:
   a computer module communicatively connectable to the clinical analytic device,
   a user operable control unit communicatively connectable to the computer module, and
   an instrument tag readable by the user operable control unit and associated with the clinical analytic device,
   wherein the user operable control unit comprises a tag reader for selecting the clinical analytic device by reading the instrument tag and is arranged to, in response to a reading of the instrument tag, cause a mode selecting signal to be transmitted to the computer module,
   wherein the mode selecting signal comprises information connected to output data protocol of the clinical analytic device, and
   wherein the computer module comprises a processor unit arranged to:
      receive the mode selecting signal;
      in response to the mode selecting signal, select an operative mode of the computer module from multiple predetermined operative modes, each of the multiple predetermined operative modes being associated with a respective clinical analytic device output data protocol; and identify test data in received data from the clinical analytic device, wherein the identification of the test data is carried out according to the selected operative mode of the computer module, the selected operative mode being associated with the clinical analytic device output data protocol.

2. The system as claimed in claim 1, wherein the user operable control unit further is arranged to, in response to a reading of the instrument tag, cause a module activating signal to be transmitted to the computer module, wherein the module activating signal comprises information connected to an identity of the computer module.

3. The system as claimed in claim 1, wherein the mode selecting signal comprises information connected to the type and/or identity of the clinical analytic device.

4. The system as claimed in claim 2 wherein the module activating signal and the mode selecting signal are one and the same signal.

5. The system as claimed in claim 1, wherein the computer module is arranged to be paired with one clinical analytic device at a time, so that the computer module can be used to indirectly address the clinical analytic device.

6. The system as claimed in claim 1, wherein the computer module further comprises a computer module tag for enabling the computer module to be individually selected by use of the control unit, in a system of multiple computer modules communicatively connected to the control unit.

7. The system as claimed in claim 6, wherein the computer module tag is attached to the computer module, and which is readable by the control unit and comprises information on identity of the computer module.

8. The system as claimed in claim 1, wherein the user operable control unit is arranged to be handheld.

9. The system as claimed in claim 1, wherein the control unit further comprises a tag reader for reading supplementary data associated with the test data, the supplementary data comprising information on one or more of the following: identity of the selected clinical analytic device, test identity data, patient identity data or sample identity data.

10. The system as claimed in claim 9, wherein the tag reader is an optical code reader, arranged to read a supplementary data tag.

11. The system as claimed in claim 1, further comprising a supplementary data tag comprising information on one or more of the following: identity of the selected clinical analytic device, test identity data, patient identity data or sample identity data.

12. The system as claimed in claim 1, wherein the computer module and the control unit are separate entities or integrated as one entity.

13. A computer module for enabling test data resulting from an analytic determination carried out on a clinical analytic device to be delivered to an electronic patient information management system, the computer module being communicatively connectable to the clinical analytic device and to a user operable control unit, wherein the computer module comprises a processor unit arranged to:

receive a mode selecting signal transmitted to the computer module by use of the control unit which reads an instrument tag associated with the clinical analytic device to select the clinical analytic device, the mode selecting signal comprising information connected to the output data protocol of the clinical analytical device;

in response to the mode selecting signal, select an operative mode for the computer module from multiple predetermined operative modes, each of the multiple predetermined operative modes being associated with a respective clinical analytic device output data protocol; and identify test data in received data from the clinical analytic device, wherein the identification of the test data is carried out according to the selected operative mode of the computer module, the selected operative mode being associated with the clinical analytic device output data protocol.

14. A computer module as claimed in claim 13, further comprising an instrument tag associated with a clinical analytic device to which the computer module is communicatively connectable to and for which the computer module comprises a compatible operative mode, the instrument tag being attachable to the clinical analytic device, wherein the instrument tag is readable by a user operable control unit, and is comprising or linking to information connected to one or more of the following: output data protocol of the clinical analytic device, identity of the clinical analytical device, type of the instrument tag.

15. A computer module as claimed in claim 13, further comprising a hub unit to which multiple computer modules and a control unit are connectable to and through which hub unit the control unit is communicatively connectable to each one of the multiple computer modules.

16. The computer module as claimed in claim 13, further comprising:
a processor unit arranged to connect and arrange supplementary data with test data according to a data protocol of the electronic patient information management system.

17. The computer module as claimed in claim 16, wherein the processor unit is arranged to receive a second mode selecting signal transmitted to the processor unit by use of the control unit, and to select the data protocol of the electronic patient information management system in response to the second mode selecting signal, wherein the second mode selecting signal comprises information connected to the data protocol of the electronic patient information management system.

18. The computer module according to claim 17, further comprising a transmitter arranged to transmit connected data to the electronic patient information management system.

19. The computer module as claimed in claim 13, further comprising a user interface communicatively connected to, and controlled by, the computer module and/or the control unit and/or the hub unit.

20. The computer module as claimed in claim 19, wherein the user interface is controlled to communicate to a user: how to next operate the control unit, and/or supplementary data that has been read or status of such data, and/or data that has been read by the tag reader or status of such data, and/or test data that has been identified by the computer module or status of such data.

21. The computer module as claimed in claim 19, wherein the user interface is controlled to request a user to accept or reject the analytic determination resulting in the test data and/or supplementary data that has been read, before allowing the test data and/or the supplementary data to be transmitted to the electronic patient information management system.

22. The computer module as claimed in claim 19, wherein the user interface is a separate unit or integrated with the computer module.

23. The computer module as claimed in claim 19, wherein the user interface is connected to the computer module.

24. A method of operating a computer module according to claim 13, the method comprising the steps of:
- receiving a mode selecting signal transmitted to the computer module by use of a control unit, which reads an instrument tag associated with a clinical analytic device to select the clinical analytic device, the mode selecting signal comprising information connected to the output data protocol of the clinical analytic device,
- selecting, in response to the received mode selecting signal, an operative mode of the computer module from multiple predetermined operative modes of the computer module, each of the multiple predetermined operative modes being associated with a respective clinical analytic device output data protocol, and
- identifying test data in received data from the clinical analytic device, wherein the identification of the test data is carried out according to the selected operative mode of the computer module, the selected operative mode being associated with the clinical analytic device output data protocol.

25. A computer program product, loadable into memory of the computer module, comprising program code for performing the steps according to the method of claim 24 when run on the computer module.

* * * * *